United States Patent
Di Carlo et al.

(10) Patent No.: US 10,613,015 B2
(45) Date of Patent: Apr. 7, 2020

(54) METHODS FOR CLASSIFICATION AND SORTING OF CANCER CELLS

(71) Applicant: THE REGENTS OF THE UNIVERSITY OF CALIFORNIA, Oakland, CA (US)

(72) Inventors: Dino Di Carlo, Los Angeles, CA (US); Soojung Hur, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 660 days.

(21) Appl. No.: 14/709,931

(22) Filed: May 12, 2015

(65) Prior Publication Data
US 2015/0308941 A1    Oct. 29, 2015

Related U.S. Application Data

(62) Division of application No. 13/284,781, filed on Oct. 28, 2011, now Pat. No. 9,090,865.
(Continued)

(51) Int. Cl.
*G01N 15/14* (2006.01)
*G01N 15/10* (2006.01)
(Continued)

(52) U.S. Cl.
CPC ........ *G01N 15/14* (2013.01); *B01L 3/502746* (2013.01); *B01L 3/502776* (2013.01);
(Continued)

(58) Field of Classification Search
CPC ..... B01L 2200/0652; B01L 2300/0864; B01L 2400/0487; B01L 3/502746;
(Continued)

(56) References Cited

U.S. PATENT DOCUMENTS

2003/0044832 A1    3/2003  Blankenstein
2003/0159999 A1    8/2003  Oakey et al.
(Continued)

FOREIGN PATENT DOCUMENTS

WO    WO 2006/057473    6/2006

OTHER PUBLICATIONS

Hur, Soojung Claire et al., Deformability-based cell classification and enrichment using inertial microfluidics, Lab on a Chip, 2011(11), 912-920.
(Continued)

*Primary Examiner* — Gautam Prakash
*Assistant Examiner* — Lydia Edwards
(74) *Attorney, Agent, or Firm* — Vista IP Law Group LLP

(57) ABSTRACT

A particle analysis system includes an inlet; an inertial focusing microchannel disposed in a substrate and having a downstream expanding region at a distal end, where the inlet is connected to a proximal end of the microchannel; a plurality of outlets connected to the microchannel at the downstream expanding region; a plurality of fluidic resistors, where each fluidic resistor is connected to a respective outlet; and a particle analyzer configured to measure a size and a position of particles in the microchannel. A particle sorting system includes an inlet; an inertial focusing microchannel disposed in a substrate and having a downstream expanding region at a distal end, where the inlet is connected to a proximal end of the microchannel; a plurality of outlets connected to the microchannel at the downstream expanding region; and a plurality of fluidic resistors, where each fluidic resistor is connected to a respective outlet.

11 Claims, 15 Drawing Sheets

Related U.S. Application Data

(60) Provisional application No. 61/408,521, filed on Oct. 29, 2010.

(51) Int. Cl.

| | | |
|---|---|---|
| *B01L 3/00* | (2006.01) | |
| *B01L 99/00* | (2010.01) | |
| *C12M 1/00* | (2006.01) | |
| *G01N 15/00* | (2006.01) | |

(52) U.S. Cl.
CPC ........ *G01N 15/10* (2013.01); *B01L 3/502761* (2013.01); *B01L 2200/0652* (2013.01); *B01L 2300/0864* (2013.01); *B01L 2400/0487* (2013.01); *C12M 47/04* (2013.01); *G01N 2015/0065* (2013.01); *G01N 2015/105* (2013.01); *G01N 2015/1006* (2013.01); *G01N 2015/1081* (2013.01); *G01N 2015/1087* (2013.01); *G01N 2015/1495* (2013.01)

(58) Field of Classification Search
CPC ........ B01L 3/502761; B01L 3/502776; C12M 47/04; F16F 2232/04; F16F 9/22; G01N 15/10; G01N 15/14; G01N 2015/0065; G01N 2015/1006; G01N 2015/105; G01N 2015/1081; G01N 2015/1087; G01N 2015/1495; G06K 9/0002; G06K 9/00053
See application file for complete search history.

(56) References Cited

U.S. PATENT DOCUMENTS

| | | |
|---|---|---|
| 2003/0219903 A1 | 11/2003 | Wang et al. |
| 2009/0014360 A1 | 1/2009 | Toner et al. |
| 2009/0286300 A1 | 11/2009 | Le Vot et al. |
| 2010/0186524 A1 | 7/2010 | Ariessohn et al. |
| 2011/0096324 A1 | 4/2011 | Watanabe et al. |
| 2011/0096327 A1 | 4/2011 | Papautsky et al. |

OTHER PUBLICATIONS

Lasko, Thomas A. et al., The use of receiver operating characteristic curves in biomedical informatics, Journal of Biomedical Informatics, 2005(38), 404-415.

Ochner, Mirjam et al., Micro-well arrays for 3D shape control and high resolution analysis of single cells, Lab on a Chip, 2007(7), 1074-1077.

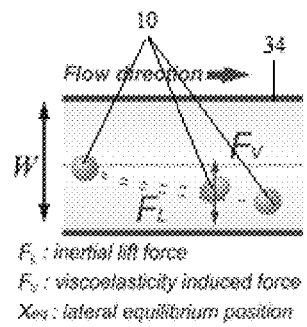
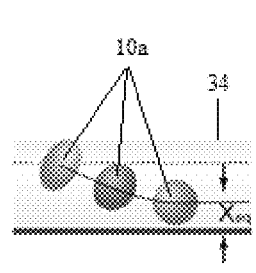
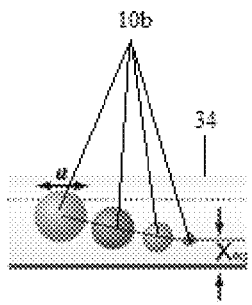
Fig. 1a  Fig. 1b  Fig. 1c
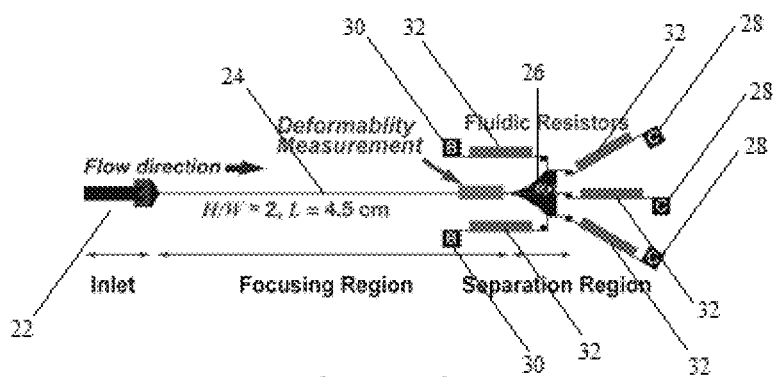
Fig. 1d
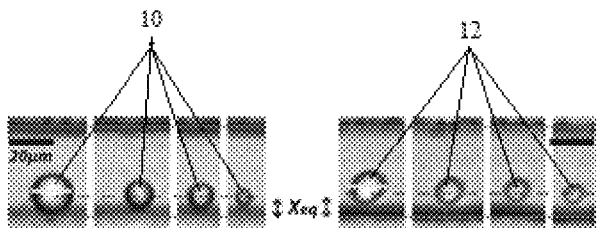
Fig. 2a  Fig. 2b

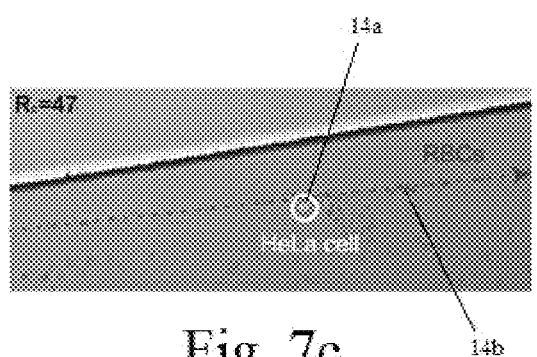 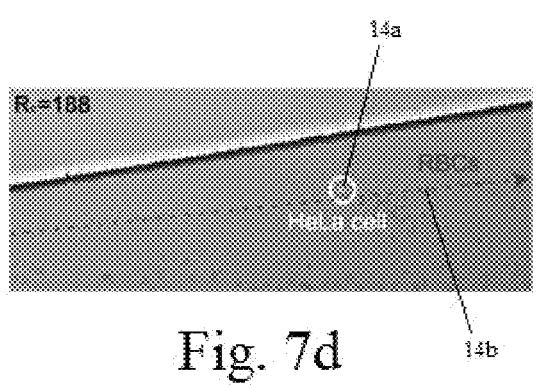
Fig. 7c     Fig. 7d
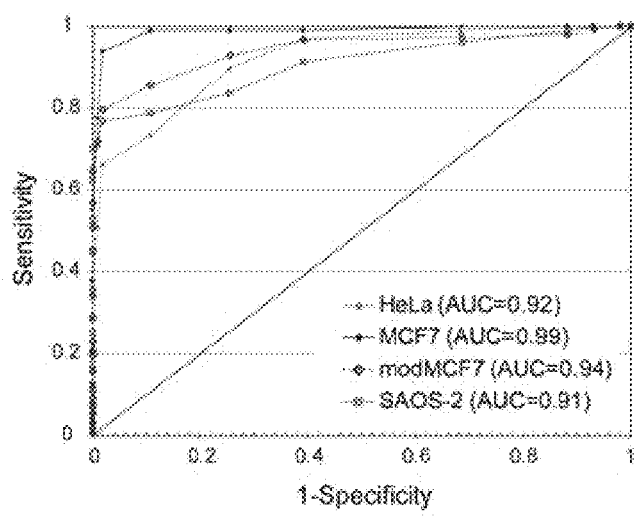
Fig. 8

Fig. 17b — Inlet
Fig. 17c — Focusing Region
Fig. 17d — Separation Region (outer outlet 1)

(inner outlet 2)

(inner outlet 3)

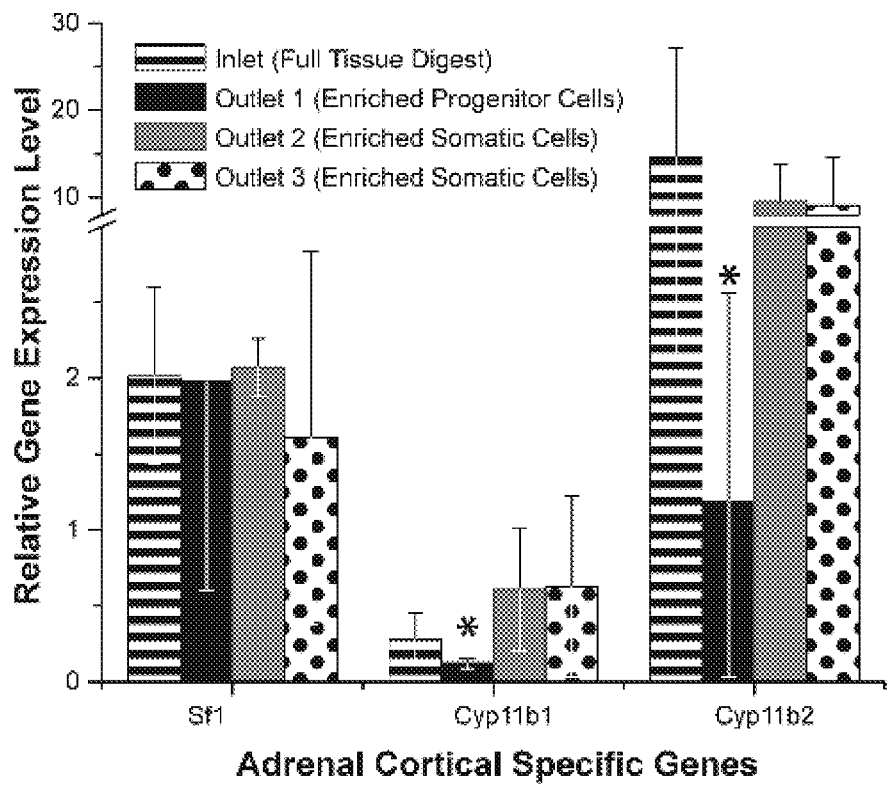
Fig. 19
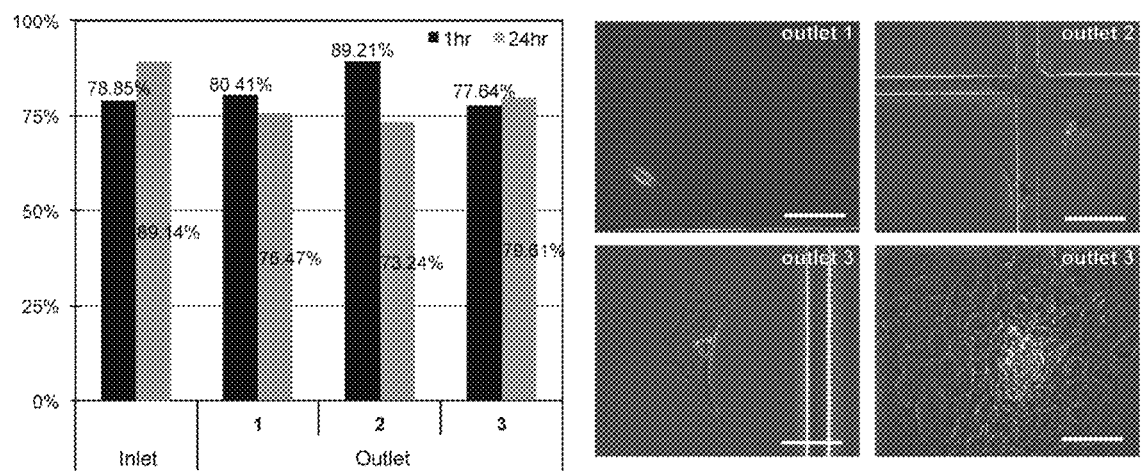
Fig. 20a
Fig. 20b

METHODS FOR CLASSIFICATION AND SORTING OF CANCER CELLS

RELATED APPLICATION

This Application is a divisional of U.S. patent application Ser. No. 13/284,781 filed on Oct. 28, 2011, now issued as U.S. Pat. No. 9,090,865, which claims priority to U.S. Provisional Patent Application No. 61/408,521 filed on Oct. 29, 2010. Priority is claimed pursuant to 35 U.S.C. §§ 119 and 120. The above-noted Patent Applications are incorporated by reference as if set forth fully herein.

STATEMENT REGARDING FEDERALLY SPONSORED RESEARCH AND DEVELOPMENT

This invention was made with Government support under 0930501, awarded by the National Science Foundation. The Government has certain rights in the invention.

FIELD OF THE INVENTION

The field of the invention generally relates to systems used to focus, separate, classify, and sort particles or cells. More particularly, the invention relates to microfluidic-based systems that focus, separate, classify, and/or sort biological materials (e.g., cells or cellular components) or particles.

BACKGROUND

The ability to detect and isolate rare target cells from heterogeneous samples is in high demand in cell biology research, immunology, tissue engineering and medicine. Techniques allowing label-free cell enrichment or detection would reduce the complexity and costs of clinical applications. Single-cell deformability has recently been recognized as a unique label-free biomarker for cell phenotype with implications for assessment of cancer invasiveness. Physical properties that define deformability include elasticity (Young's Modulus) for solid particles, and viscosity, viscosity ratio and surface tension for droplets.

Alteration in the deformability (or mechanical stiffness) of single cells has been identified to be a useful indicator of changes in cellular phenotype of importance for biological research. Various diseases are associated with cell deformability alterations including cancer, blood diseases (sickle cell anemia, hereditary spherocytosis, and immune hemolytic anemia), and inflammation. In particular, the stiffness of individual cancer cells has been found to be drastically reduced when compared to normal tissue of the same origin. Further, decreasing single-cell stiffness was correlated with increasing invasiveness or metastatic potential. Biomechanical assays confirmed this correlation both with in vitro human cancer cell lines as well as clinical biopsies. Moreover, pluripotent stem cells are more deformable than differentiated cells. Differentiated cells with different lineages will have different deformability. Cells that are responding to anti-cancer drugs have changes in deformability as well.

These results are practically important considering the simplicity and low potential cost for obtaining label-free biophysical measurements. A label-free deformability biomarker would likely have lower operating costs than current molecular-based biomarkers that require pre-processing steps, dyes, and/or costly antibodies. Furthermore, disease states of interest can be expanded to those without predetermined immunological markers as long as a correlation between deformability phenotype and clinical outcome is confirmed. Specifically, deformability-based target cell classification/enrichment would be useful for cancer research and diagnostics since it would enable controlled experiments correlating cell mechanics of cancer cell lines with known genetic defects as well as analysis of malignant cells of unknown origin (e.g. circulating tumor cells ("CTCs") in peripheral blood or malignant cells in biopsy samples) for cancer staging, relapse detection, molecular analysis of cancer drug resistance, and potentially early detection.

In the short term, a simple point-of-care clinical device for enumeration of CTCs reduces the barrier for routine use. Identification of the number of CTCs in blood has been shown to be predictive of cancer prognosis and may suggest more or less aggressive treatment regimes. It also has potential for characterizing the efficacy of a particular chemotherapeutic therapy. Additionally, if genetic information about the primary tumor can be collected, this will allow non-invasive molecular biopsies of the primary cancer site that can indicate if the cancer is susceptible or has become resistant to specific drugs.

In the long term, isolation of populations of CTCs could allow molecular analysis to uncover new markers that are expressed in the unique deformable subset of tumor cells that may assist in diagnosis or understanding of the disease. In addition, if sensitivity and specificity is high enough, CTC analysis might make it possible to detect cancer early in pre-symptomatic patients or those who are at risk for relapse with a simple noninvasive blood test, leading to a decrease in cancer deaths.

Current techniques developed for measuring deformability and elastic properties of cells include micropipette aspiration, atomic force microscopy, optical deformability, magnetic bead twisting assays, and optical tweezers. Cell elastic constants (E) from 0.05-30 kPa have recently been measured by atomic force microscopy. Despite the success in obtaining overall deformability measurements for cells of interest, the low throughput (1 cell/min-1 cell/sec) of current cell deformability measurement techniques renders current technologies ill-suited for statistical analysis of large heterogeneous biological samples or rare cell detection. For example, current throughput does not allow routine screening of millions of cells, which is often desired for statistically robust diagnostic and research applications (e.g., detection/enumeration of cancer cells in blood or biopsies). Moreover, post-measurement enrichment of cell populations with uniform deformability has not been demonstrated for current technologies although high-purity isolation of viable cells with preserved gene expression profiles would facilitate the comprehensive assessment of single-cell mechanics correlated with unexplored genes responsible for such changes in phenotype. Further, many of these techniques are expensive because they are complicated or not passive.

Current techniques to isolate and enumerate rare cancer cells have shown promise for patient prognosis and treatment monitoring. In fact, the CTC detection system by Veridex Corp. was selected as the Top Medical Breakthrough for 2009 by the Cleveland Clinic. Unfortunately, current technologies have relatively low throughput (~3-8 mL of blood/hr) and thus would be effective for early detection applications due to the very low number of CTCs in blood (<1 part per billion). Additionally, current techniques require immuno-labeling with magnetic beads and fluorescent markers which adds a large additional cost.

Novel techniques allowing deformability activated target cell/particle enrichment and/or high-throughput deformability measurement of individual cells would expand the research use and clinical adoption of this biomarker. Accordingly, there is a need for systems and methods for high-throughput deformability-based cell/particle categorization and sorting.

SUMMARY

In one embodiment, a particle sorting system includes an inlet; an inertial focusing microchannel disposed in a substrate and having a downstream expanding region at a distal end, where the inlet is connected to a proximal end of the microchannel; a plurality of outlets connected to the microchannel at the downstream expanding region; and a plurality of fluidic resistors, where each fluidic resistor is connected to a respective outlet. Optionally, the inlet includes a filter. In some embodiments, the inertial focusing microchannel is a substantially straight microchannel. In other embodiments, the inertial focusing microchannel has a substantially rectangular cross-section having a height and a width. In some of those embodiments, a ratio of the height to the width is approximately 3:2 to 4:1. In other embodiments, a ratio of the height to the width is approximately 2. In still other embodiments, the ratio of the height to the width is at least 2. In yet other embodiments, the height is approximately 85 μm and the width is approximately 38 μm. In still other embodiments, the inertial focusing microchannel has an axial length of approximately 4.5 cm.

Alternatively or additionally, the downstream expanding region expands in a plane substantially parallel to the width of the cross section. In some embodiments, the downstream expanding region has a side wall and a longitudinal axis, and where an angle between the side wall and the longitudinal axis increases in a downstream direction. In some of those embodiments, the angle increases at a rate of approximately 2° per 100 μm along the longitudinal axis. Optionally, multiple (e.g., five outlets) are connected to the microchannel at the expanding downstream region, including three inner outlets flanked by two outer outlets. In other embodiments, each fluidic resistor includes a serpentine channel having a plurality of turns. In some of these embodiments, each fluidic resistor includes approximately 20 turns and each fluidic resistor has a total channel length of approximately 3 cm. The system may also include a pressure/flow source configured to drive a particle containing fluid through the inertial focusing microchannel. In some embodiments, where the system is configured to sort at least two types of particles, the microchannel has width W and the two types of particles have respective diameters $a_1$ and $a_2$, such that each of $a_1$ and $a_2$ is between 20% and 70% of W. In other embodiments, the system may be configured to sort at least two types of particles with different deformabilities and/or sizes.

In an alternative embodiment, a particle sorting system includes an inlet; a plurality of inertial focusing microchannels disposed in a substrate, each having a downstream expanding region at a distal end, where the inlet is connected to a proximal end of at least one of the microchannels; three inner outlets flanked by two outer outlets, where each outlet is connected to each microchannel at the respective downstream expanding regions; and a plurality of fluidic resistors, where each fluidic resistor is connected to an outlet. Optionally, the inlet is connected to each of the plurality of inertial focusing microchannels at a respective proximal end of the microchannel. Alternatively or additionally, a proximal end of at least one inertial focusing microchannel is connected to an outlet of another inertial focusing microchannel. In some embodiments, the plurality of inertial focusing microchannels is arranged in a ring with the inlet at the center. The ring may include multiple pluralities of inertial focusing microchannels, where each plurality of microchannels is arranged in a concentric loop. The ring may also include concentric ring-shaped reservoirs connected to outlets. Also, the ring may include an outer concentric ring-shaped reservoir connected to inner outlets.

In another embodiment, a method of sorting at least two types of particles suspended in a fluid includes flowing unprocessed fluid having particles suspended therein through a particle sorting system, including an inertial focusing microchannel disposed in a substrate and having a downstream expanding region at a distal end, at least one inner outlet and two outer outlets, where each outlet is connected to the microchannel at the downstream expanding region, and a plurality of fluidic resistors, where each fluidic resistor is connected to a respective outlet; collecting processed fluid samples having particles suspended therein from each of the respective outlets, where each processed fluid sample is enriched in one type of particle compared to the unprocessed fluid. In some embodiments, collecting processed fluid samples includes collecting fluid samples enriched in more deformable particles at the inner outlet. In other embodiments, collecting processed fluid samples includes collecting fluid samples enriched in larger particles at the inner outlet. Optionally, the microchannel has width W and the two types of particles have respective diameters $a_1$ and $a_2$, such that each of $a_1$ and $a_2$ is between 20% and 70% of W. Alternatively or additionally, the microchannel has width W, and the fluid has density $\rho$, maximum velocity $U_m$, and viscosity $\mu$, and where the unprocessed fluid is flowed through the particle sorting system at a flow rate such that channel Reynolds number, $R_c = \rho U_m W / \mu$, is between 10 and 40. In some embodiments, the flow rate is approximately 60 μl/ml and the $R_c$ is approximately 21.

In yet another embodiment, a method of determining a deformability of particles includes flowing a fluid having particles suspended therein through an inertial focusing microchannel disposed in a substrate; measuring a size of the particles; measuring a position of the particles in microchannel; and calculating a deformability of the particles based on the measured size and the measured position in the microchannel. In some embodiments, calculating a deformability of the particles includes calculating a deformability of the particles from the measured position for the measured size. In other embodiments, calculating a deformability of the particles includes comparing the measured position to a position of droplets with a known viscosity to calculate an effective viscosity of the particles. Calculating a deformability of the particles may also include plotting the measured size and measured position of each particle in a scatter plot, and analyzing the scatter plot.

In still another embodiment, a particle analysis system includes an inlet; an inertial focusing microchannel disposed in a substrate, where the inlet is connected to a proximal end of the microchannel; an outlet connected to the microchannel at the downstream region; and a particle analyzer configured to measure a size and a position of particles in the microchannel.

BRIEF DESCRIPTION OF THE DRAWINGS

FIG. 1a is a diagrammatic view of a deformable particle flowing through a microchannel.

FIG. 1b-FIG. 1c are diagrammatic views of deformable (FIG. 1b) and rigid (FIG. 1c) particles of various diameters flowing through a microchannel.

FIG. 1d is a top schematic view of an inertial focusing microchannel according to one embodiment of the invention.

FIG. 2a-FIG. 2b are high-speed microscopy images of relatively rigid (FIG. 2a) and deformable (FIG. 2b) particles flowing through a microchannel.

FIG. 7c-FIG. 7d are high-speed microscopy images of cancer cells and blood cells flowing through a microchannel.

FIG. 8 is a receiver operating characteristic (ROC) curve graphically representing the sensitivity and specificity of one embodiment of the invention for cancer cell classification from blood samples.

FIG. 16b is a bar graph plotting the relative OCT4 expression level of cells collected from each outlet of the device depicted in FIG. 16a.

FIG. 17b-FIG. 17d are detailed top schematic views of various portions of the inertial focusing microchannel of FIG. 17a.

FIG. 18a-FIG. 18c are fluorescent microscopy images of cells collected at various outlets of the device in FIG. 17a.

FIG. 19 is a bar graph showing the relative gene expression levels of various adrenal cortical specific genes for various samples related to the device in FIG. 17a.

FIG. 20a is a bar graph of the results of colorimetric viability tests for various samples related to the device in FIG. 17a.

FIG. 20b is a series of four bright field images of 10 day cultured cells that have been flowed through the device in FIG. 17a.

DETAILED DESCRIPTION OF THE ILLUSTRATED EMBODIMENTS

Figure 2C:
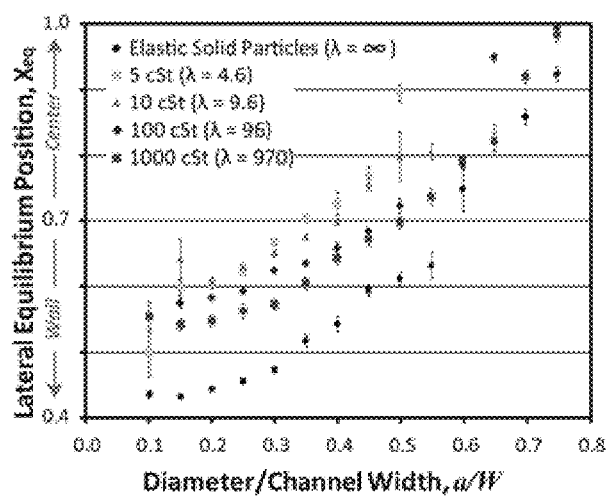
FIG. 2c is a scatter plot graph of lateral equilibrium position against particle diameter/channel width.

High-throughput, continuous, passive, and label-free cell classification and enrichment based on cell size and deformability is achieved using a unique combination of fluid dynamic effects in a microfluidic system. The disclosed system takes advantage of a balance between deformability-induced and inertial lift forces as cells travel in a microchannel flow. Particles and droplets with varied elasticity and viscosity have distinct lateral dynamic equilibrium positions due to this balance of forces. This system classifies various cell types using cell size and deformability as distinguishing markers. Further, using differences in dynamic equilibrium positions, the system also performs passive, label-free and continuous cell enrichment based on these markers, enabling off-chip sample collection without significant gene expression changes. The disclosed method allows for high-throughput deformability measurements and cost-effective cell separation to obtain viable target cells of interest in cancer research, immunology, and regenerative medicine.

Inertial Focusing of Deformable Particles in Poiseuille Flow.

Inertial effects in microfluidic systems have the ability to easily focus and order particles and cells continuously without external forces. In brief, an inertial lift force, $F_L$, induces lateral migration of particles in confined flow (see FIGS. 1a-FIG. 1c) and creates distinct inertial lift focusing positions at finite particle Reynolds numbers, $$R_P = \frac{\rho_{ex} U_{max} a^2}{\mu_{ex} D_h} = R_C \left(\frac{a}{D_h}\right)^2.$$

Here, $\rho$, $U_{max}$, $\mu_{ex}$, $R_C$, $a$ are the density, the maximum velocity, the dynamic viscosity of the continuous phase fluid, the channel Reynolds number, and the particle diameter, respectively, while $D_h$ is the hydraulic diameter of the channel, defined as $$D_h = \frac{2WH}{W+H}$$

where W and H are the channel width and height, respectively. Particles/cells can be inertially focused at two distinct lateral focusing positions and one uniform z-position using high aspect ratio channels (2<H/W). These channels reduced the probability of particle overlap and out-of-focus blur and provided similar cell signature images, allowing accurate cell-type classification with extreme throughput. These high-aspect ratio channel structures are used to focus cells to two lateral positions.

In addition to nonlinearity associated with the inertia of the fluid, nonlinear lateral migration can occur when the particle itself is deformable. Early theoretical investigations reported that elastic solid particles experience a force away from the wall in Poiseuille flow, such that particles laterally migrated to the channel centerline, even in the zero-Reynolds-number limit. Lateral migration of deformable particles results from a nonlinearity caused by matching of velocities and stresses at the particle/droplet interface. That is, the magnitude of lateral drift velocity and lift force is closely related to the deformed shape of the object. For droplets with surface tension, σ, the Weber, $$We = \frac{\rho_{ex} U_{max}^2 a}{\sigma},$$

or capillary, $$Ca = \frac{\mu_{ex} U_{max} a}{\sigma W}$$

umber provides a dimensionless parameter (inertial stress vs. surface tension or viscous stress vs. surface tension) that characterizes the relative deformation expected for a droplet. The internal to external viscosity ratio, $\lambda=\mu_{in}/\mu_{ex}$, is another significant parameter characterizing droplet deformation and drift. The drift velocity (i.e., lift force) increases with the droplet deformability and the direction of migration is predominantly toward the channel centerline for all deformable objects. A notable exception to this trend, and migration towards the wall, was observed with viscous droplets when the viscosity ratio ranged between 0.5 and 10.

The fact that deformable particles experience an additional lift force can be used in high throughput deformability-induced particle classification and separation. Deformation-induced lift forces will act in superposition with inertial lift forces to create modified lateral equilibrium positions that are dependent on particle deformability. Consequently, the lateral equilibrium position can then be used as the measure of particle deformability when the particle size is taken into account. Furthermore, the differences in lateral equilibrium position among cell types can be utilized for deformability-induced target cell enrichment by directing entrained target cells to separate designated outlets.

Figure 12A:
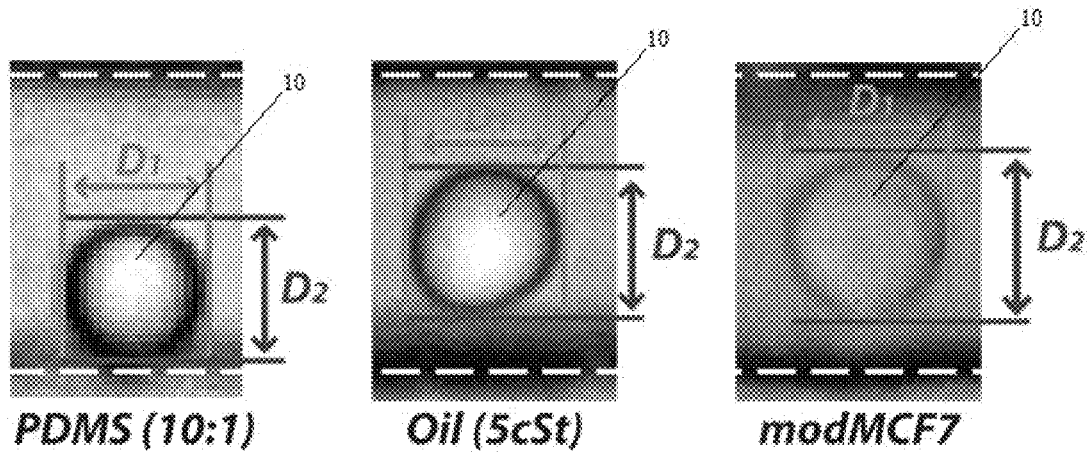
FIG. 12a-FIG. 12b are high-speed microscopy images of particles flowing through a microchannel.
Figure 12B:
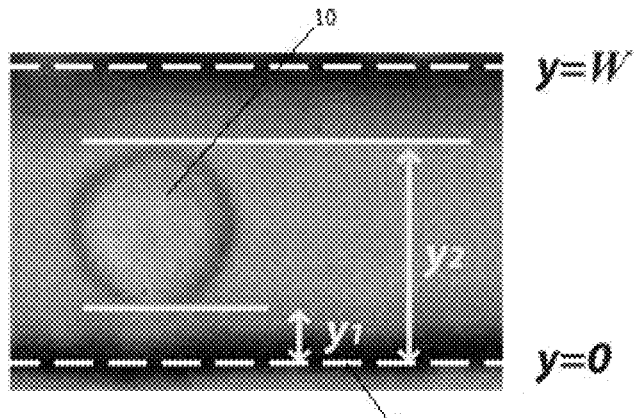

FIG. 1a-FIG. 1c show the forces acting on deformable cells and particles flowing through microchannels. FIG. 1a illustrates the balance between two lateral forces, namely inertial lift force, $F_L$, and viscoelasticity induced force, $F_v$, which leads to unique lateral inertial focusing equilibrium positions, $X_{eq}$, for deformable particles 10a (FIG. 1b) and rigid particles 10b (FIG. 1c) with various diameters, a. Diameter, a, of particles 10, droplets 12, and cells 14 can be determined by measuring and averaging the distance between outer edges of particulates in lateral ($D_1$) and vertical ($D_2$) directions, as shown in FIG. 12a (a=($D_1$+$D_2$)/2). Lateral equilibrium positions of flowing particles 10 and cells 14 can be determined from the distance of the center position from the wall 16, as shown in FIG. 12b ($X_{eq}$=($y_1$+$y_2$)/2).

Figure 2D:
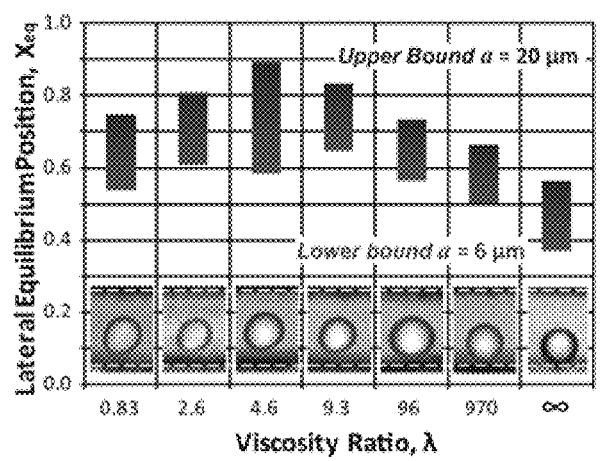
FIG. 2d is a bar graph of lateral equilibrium position against viscosity ratio.

FIG. 2a-FIG. 2d show particle viscoelastic properties affecting lateral equilibrium position. FIG. 2a-FIG. 2b are high-speed microscopic images of elastic solid particles 10 (i.e., relatively rigid; FIG. 2a) and viscous oil droplets 12 (i.e., highly deformable; FIG. 2b) of various sizes. $X_{eq}$ for viscous oil droplets 12 and elastic particles 10 varies as a function of particle diameter to channel width, a/W (FIG. 2c), and viscosity ratio, λ (FIG. 2d). Error bars in FIG. 2c indicate the standard error and λ is the ratio between the dynamic viscosity of oil and water at 25° C. The bars in FIG. 2d represent the range of equilibrium position measurements for particles 10 and oil droplets 12 whose diameters range from 6 μm (bottom) to 20 μm (top).

Figure 6A:
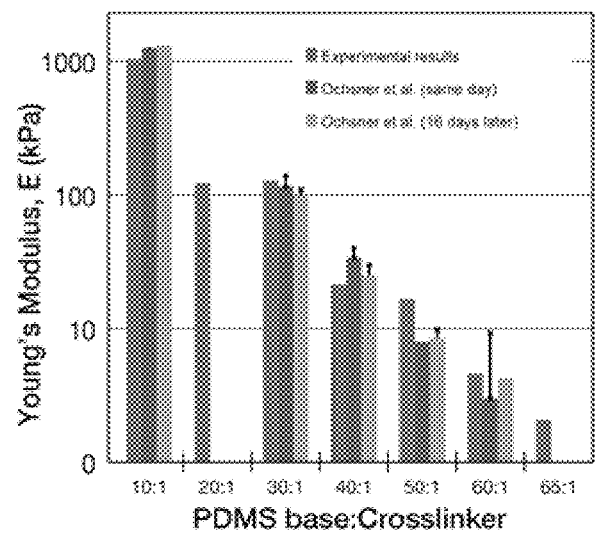
FIG. 6a is a bar graph of Young's Modulus of various mixtures of PDMS base and crosslinker.
Figure 6B:
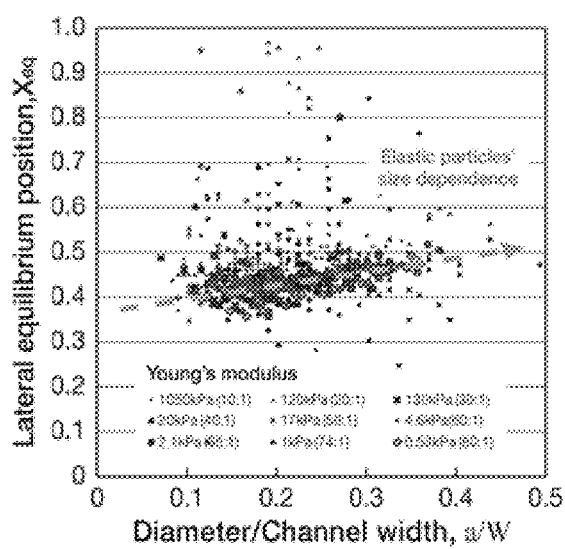
FIG. 6b is a scatter plot of lateral equilibrium position against cell diameter/channel width.

FIG. 6a-FIG. 6b illustrate Young's Modulus of PDMS particles and its effect on lateral equilibrium position. FIG. 6a shows that the elasticity of bulk PDMS specimens is controlled by varying crosslinker density. The Young's modulus of PDMS specimens having varying amounts of crosslinker density was measured using the standard tensile test (Instron 4111, elongation rate at 0.5 mm/min) The measured values were in good agreement with those reported in *Micro-well arrays for 3D shape control and high resolution analysis of single cells*, Ochsner M., Dusseiller M. R., Grandin H. M., Luna-Morris S., Textor M., Vogel V., and Smith M. L., Lab on a Chip, 2007(7), 1074-1077. FIG. 6b shows that the inertial focusing equilibrium positions ($X_{eq}$) of PDMS particles (2<a<30 μm) depends on particle size but is independent of elasticity over the range tested. Presumably, the deformation of elastic solid particles was not sufficient to induce the lateral migration force.

Device Design and Fabrication

In a system for cell classification, a straight high aspect ratio channel (W=38 μm, H=85 μm, and L=4.5 cm) includes one inlet with coarse filters and one outlet. Particle/cells are inertially focused to two lateral focusing positions at a uniform z-plane in the channel, which is also known as a microchannel. The inertial focusing straight channels advantageously have an aspect ratio (ratio between channel width to height) equal or similar to 2.

In a system for cell enrichment, a Deformability Activated Cell Sorting (DACS) microfluidic device 20 includes one inlet 22 with coarse filters (not shown), a straight focusing channel 24 (W=40 μm, H=90 μm, and L=4.5 cm), a gradually expanding region 26, and 5 branched outlets 28, 30 with fluidic resistors 32 (see FIG. 1d). A gradually expanding region maintains focused cells in the focusing streamline while enhancing the $X_{eq}$ differences between cell types when compared to straight angled expansions (See, FIGS. 7c-7d). Particles 10 flowing through a microchannel 34 having a rectangular cross section localize to discrete positions along the width, W, of the cross-section, and localize to one position along its length, L. Accordingly, the expanding region 26 expands in a plane substantially parallel to the width, W, to enhance the $X_{eq}$ differences in that direction. The expanding region 26 is formed by gradually increasing the angle between the channel wall 16 and the flow direction 36 by 2° per 100 μm.

Each outlet has a fluidic resistor attached in order to minimize the flow ratio distortion due to any small variation in the fluidic resistance at the outlet (e.g. small variation in tubing length or small debris partially clogging one or more outlets). Each fluidic resistor may be a serpentine channel with about 20 turns, and a total resistant channel length of about 3 cm although other dimensions may be used. The resistors increase the overall fluidic resistance in the system to minimize the effect of small resistance variations due to tubing imperfections and debris. The fluidic resistors keep the splitting ratios more constant, resulting in a more consistent, longer lived system.

The optimum flow rate is around 60 μl/min ($R_c$=21) for this configuration. This flow rate provides sufficient overall system throughput and target cell yield. Cancer cell recovery is around 96% and 79% for $R_c$ equal to 21 and 42, respectively for metastatic breast cancer cells.

FIG. 1d schematically depicts a microfluidic device used for cancer cell enrichment based on these parameters. The microfluidic device consists of an inlet 22 with a coarse filter, a straight focusing (40×90 μm) region 24, and a gradually expanding separation region 26 ending in multiple branched outlets with high fluidic resistance. Five (5) such outlets, denoted as B or C, represent the designated collection outlets for sampled enriched for blood cells (B) and cancer cells (C), respectively in enrichment devices. All schematics represent the top view of the microfluidic device.

Figure 7A:
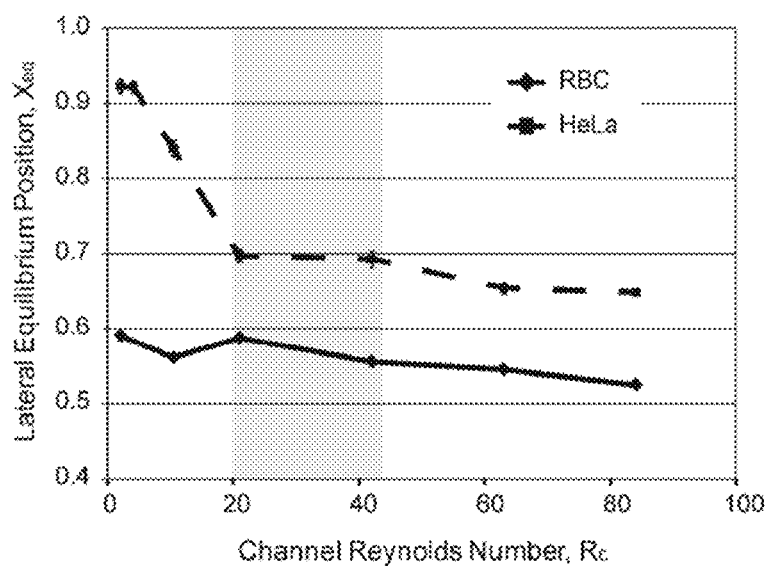
FIG. 7a is a line graph of lateral equilibrium position against channel Reynolds number.
Figure 7B:
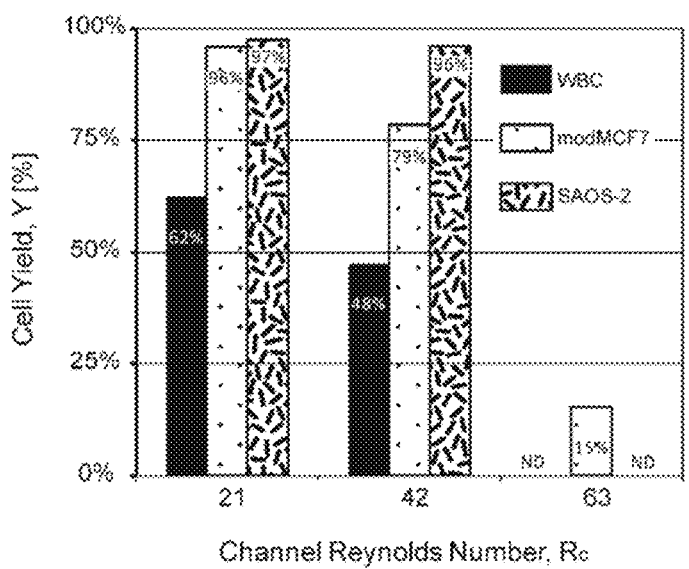
FIG. 7b is a bar graph of cell yield against channel Reynolds number.

FIGS. 7a-7d depict the results of empirical studies to determine optimum conditions for label-free cancer cell enrichment based on cell deformability using the DACS device. FIG. 7a shows that the lateral equilibrium position of human red blood cells and HeLa cells shifts toward the wall with increasing channel Reynolds number, $R_c$. The error bars indicates the standard error of the mean (N=100). FIG. 7b is a bar graph plotting the number of cells collected at cancer (three inner) outlets at three different channel Reynolds numbers, $R_c$. FIG. 7b shows that the number of cells collected decreases as $R_c$ increases. The yield of WBC and SAOS-2 collected at $R_c$=63 was not determined (marked as ND) since that of modMCF7 was found to be impractical for enrichment purposes. Accordingly, optimum operating conditions (shadowed region in FIG. 7a) that would allow for maximum cancer cell enrichment in blood was determined to be in a range between 20<$R_c$<42. FIG. 7c shows that more deformable cancer cells 14a, initially focused closer to the channel centerline in the straight channel, remained closer to the channel centerline than blood cells 14b at the expanding outlet. FIG. 7d shows that cancer cells 14a and blood cells 14b, however, had unexpected but distinct paths at the expanding outlet when the mixture was injected at higher rates, demonstrating the importance of the outlet geometry.

Figure 15:
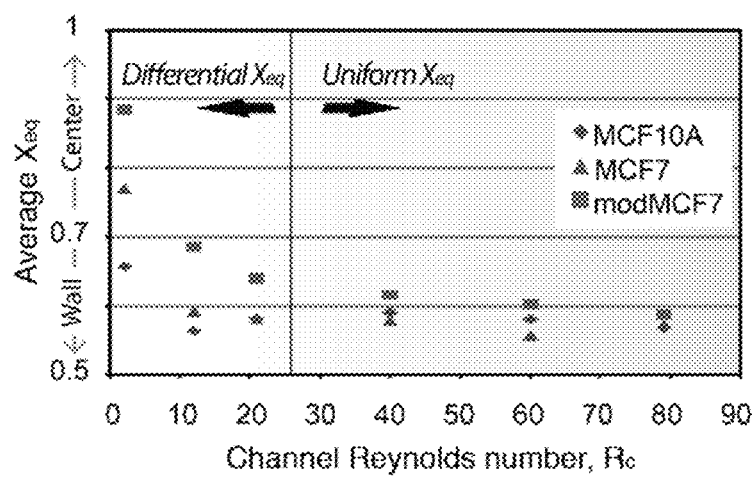
FIG. 15 is a graph of lateral equilibrium position against channel Reynolds number.

The optimal $R_c$ varies depending on the application. For instance, when separating cells having similar diameters, such as malignant breast cancer cells (e.g., MCF7 and modMCF7) and healthy breast tissue cells (e.g., MCF10A), deformability induced lift forces are mainly responsible for cell separation. Accordingly, the optimal $R_c$ is about 20 for samples containing cells with very similar sizes but varying deformability. At higher $R_c$ (e.g., $R_c$>about 27), associated with higher flow rates, fluid inertia effects dominate, and all cell types of a similar diameter, regardless of their mechanical properties, tightly focus at a single lateral equilibrium position. FIG. 15, in which the lateral equilibrium position, $X_{eq}$, of breast epithelial cells (MCF10A) and benign (MCF7) and invasive breast carcinoma cells (modMCF7, chemically modified) varies as flow rate (and $R_c$) increases, demonstrates this effect.

The microfluidic devices can be fabricated with conventional soft lithography techniques using PDMS. In brief, the mold is fabricated by spin-coating a negative photoresist (KMPR 1050™, Microchem) on a 4" silicon wafer to obtain desired height of microfluidic channels (85 or 93 μm). PDMS (SYLGARD 184™, Dow Corning) is cast onto the prepared mold and degassed. Inlet and outlets of the devices are punched in the cured PDMS cast with a pin vice (Pin vise set A, Technical Innovation, Inc.) and bonded to slide glass using air plasma (Plasma Cleaner, Harrick Plasma).

Inertial Focusing, High Speed Imaging, and Categorization of Deformable Particles and Cells The lateral equilibrium positions of various particles/cells can be assayed by individually injecting solutions containing the particles/cells through a single straight channel with high aspect ratio (i.e., W:H≈1:2). Flowing particles can be inertially focused to distinct lateral and vertical positions when the diameter of the particle ranges between 20 and 70% of the channel width. Assayable particles and cells include, but are not limited to, PDMS particles, viscous oil droplets, red blood cells, peripheral blood mononuclear cells, and benign and metastatic cancer cells (such as HeLa, MCF7, SAOS-2, and modMCF7). Blood samples can be prepared by drawing into venous blood collection tubes (BD Vacutainer®) containing 0.4 mL of trisodium citrate (13.2 g/L), citric acid (4.8 g/L) and dextrose (14.7 g/L).

Microparticle/cell containing samples are injected into the microchannel of the cell classification system with a syringe pump (PHD 2000™, Harvard Apparatus) equipped with a 10 mL glass syringe (Hamilton) to sustain an overall flow rate, Q, between 25 μl/min and 450 μl/min. The solution in a vertically oriented glass syringe is continuously agitated during injection in order to maintain a uniform concentration throughout the process. The loaded syringe is connected to $\frac{1}{32}$×0.02" PEEK tubing (Upchurch Scientific) by a ½" Luer stub (Instech Solomon) and tubing is secured in the punched inlet and outlet of the microfluidic device.

High-speed microscopic images of inertially focused cells/particles are recorded downstream using a PHANTOM™ v7.3 high speed camera (Vision Research Inc.) and PHANTOM CAMERA CONTROL™ software. High speed images are taken using 1 μs exposure time and image intervals are varied according to the flow rate. The lateral equilibrium position ($X_{eq}$) of individual particles/cells is determined by measuring the distance between the particle center and the channel wall ($X_{eq}$ equal to 0 or 1 indicates that a particle was centered at the channel wall or centerline, respectively) with the aid of high-speed microscopy and image viewer software (IRFANVIEW). More than 100 $X_{eq}$ data points can be taken for each individual particle/cell type in order to obtain clear statistical insight. The maximum and average standard error for each averaged $X_{eq}$ data point is 0.07 and 0.01, respectively.

Lateral Equilibrium Position is a Function of Particle Viscoelastic Properties.

The lateral equilibrium position ($X_{eq}$) of particles and viscous droplets strongly depends on particle size and viscosity (See FIG. 2a and FIG. 2b). For instance, compared to the baseline equilibrium positions of rigid PDMS particles (elasticity over a range of 0.5-1000 kPa, see FIG. 6a) deformable droplets occupy equilibrium positions much closer to the channel centerline (FIG. 2c). Additionally, the droplets shift toward the channel-center as viscosity decreased (from 1000 to 5 cSt). For lower viscosities, droplets adopt more deformed shapes at steady state (FIG.

2d), which is associated with increased deformation-induced lift. Accordingly, lateral force is inversely related to droplet viscosity ratio.

Moreover, the shape of droplets with lower viscosity (λ<10) exhibits a larger curvature near the channel wall, because the surface of the droplet near the wall experiences larger stresses. As the viscosity decreases below 5 cSt (λ<4.6), the lateral equilibrium position again moves closer to the channel wall (FIG. 2(d)) despite the similarity in the droplet shape. This phenomenon may indicate a shift in the direction of deformability-induced migration as a function of internal to external viscosity ratio, λ.

Lateral Equilibrium Position of Cells Used for Classification of Cell Type.

Figure 3A:
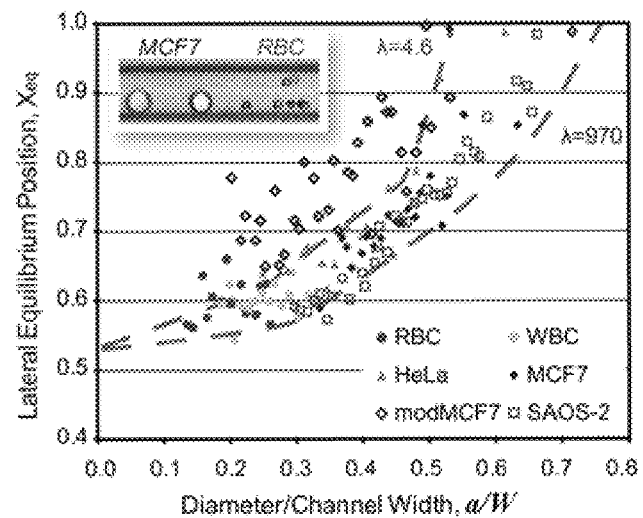
FIG. 3a is a scatter plot graph of lateral equilibrium position against cell diameter/channel width.
Figure 3B:
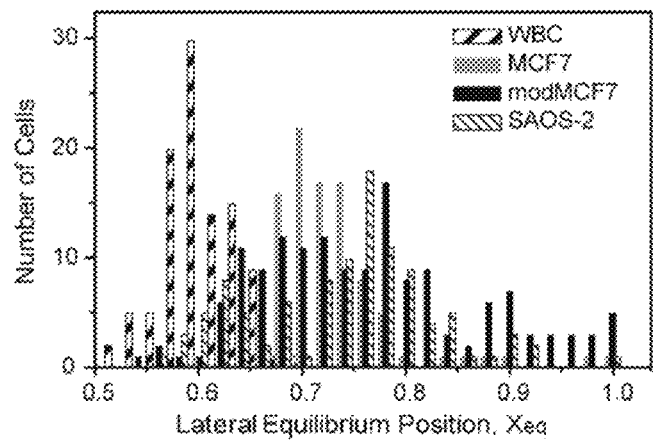
FIG. 3b is a histogram of the number of cells at a lateral equilibrium position.

Cells migrate to positions closer to the channel centerline than rigid particles, behaving in a similar manner to viscous droplets. As shown in FIG. 3, $X_{eq}$ for cells, including blood (erythrocytes and leukocytes), carcinoma (HeLa and MCF7) and osteosarcoma (SAOS-2) cells, follow a comparable trend to that of viscous droplets (4.6<λ<970). Breast cancer cells with increased metastatic potential (i.e. modMCF7 cells) migrate even closer to the centerline than benign breast cancer cells (MCF7) despite the similarity in cell diameter range (see FIG. 3a). In general, cancer cells are distinguishable from blood cells based on their size and equilibrium positions. In a histogram of $X_{eq}$ for leukocytes, breast cancer cells and osteosarcoma cells, more than 97% of cancer cells have $X_{eq}$ greater than 0.6 (see FIG. 3b). Accordingly, successful gating (0.6<$X_{eq}$) would enable cancer cell detection with high sensitivity and specificity in a mixed dilute blood sample (for example in detection of circulating tumor cells). The combination of cell size and deformability can be used as a biomarker for metastatic cells.

Figure 3C:
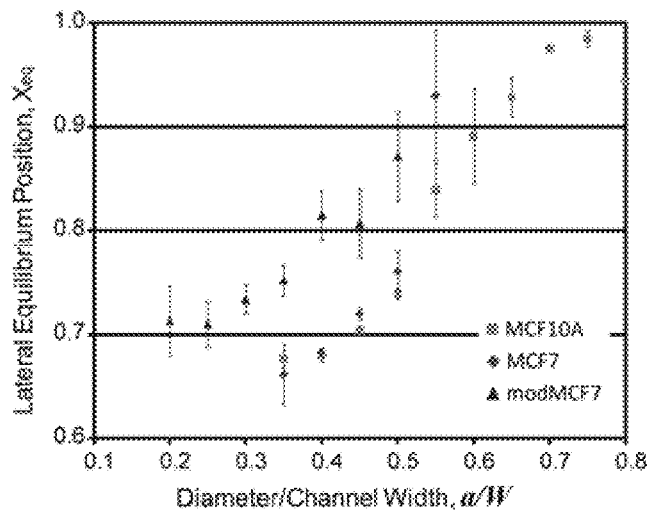
FIG. 3c is a scatter plot graph of lateral equilibrium position against cell diameter/channel width.

FIG. 3a-FIG. 3c illustrate that lateral equilibrium positions, $X_{eq}$ and size of cells is indicative of cell type. FIG. 3a is a graph that plots the $X_{eq}$ of blood cells, carcinoma, and osteosarcoma cells as a function of cell diameter to channel width ratio, a/W at $R_c$=21. FIG. 3b is a histogram of $X_{eq}$ for leukocytes, MCF7 cells, modified MCF7 cells and SAOS-2 cells at $R_c$=21. The histogram shows that using a cut-off for $X_{eq}$ at 0.6 yields high sensitivity and specificity classification of cancer cells amongst leukocytes (see, FIG. 7a). FIG. 3c plots averaged $X_{eq}$ of normal (MCF10A), benign (MCF7) and malignant breast epithelial cells (modMCF7) as a function of cell diameter to channel width ratio, a/W at $R_c$=21. FIG. 3c illustrates the use of this system for classification of tumor cell invasiveness. Error bars in FIG. 3c indicate the standard deviation.

A receiver operating characteristic curve (ROC) shows the degree of sensitivity and specificity of this cell classification system for detecting cancer cells amongst a blood cell population. An area under this curve (AUC) greater than 0.91 (which is high) was attained for several cancer cell lines tested (see FIG. 8), showing that this system is a high sensitivity and specificity indicator for cancer cells in blood. The AUC was determined using the empirical method.

FIG. 8 is a receiver operating characteristic (ROC) curve graphically representing the sensitivity and specificity of the technique, disclosed herein, for cancer cell classification from blood samples. Each point on the ROC curve corresponds to a unique lateral equilibrium position threshold (0.4<$X_{eq}$<1 with 0.02 interval). Full area under the ROC curve (AUC), the accuracy index of the technique, was determined using the empirical method described in *The use of receiver operating characteristic curves in biomedical informatics*, Lasko T., Bhagwat J., Zou K., and Ohno-Machado L., *Journal of Biomedical Informatics*, 2005(38), 404-415. A detection technique with perfect sensitivity and specificity would have an AUC value equal to 1. A high AUC (greater than 0.91) was attained for all cancer cell types.

Moreover, the lateral equilibrium position of malignant cancer cells (modMCF7) is distinctively different from those of benign cancer cells (MCF7) and normal tissue cells (MCF10A) from the same origin (see FIG. 3c). Accordingly, $X_{eq}$ can also be used to determine cancer invasiveness or stage from disaggregated biopsy samples. Additionally, the technique holds promise for other cases where deformability changes accompany phenotypic changes, for example in assaying the level of leukocyte activation or degree of embryonic stem cell differentiation. A combination of cell size and $X_{eq}$ measurements provides a unique cellular signature, allowing automatic target cell enumeration through image-based or other optical detection approaches. Further, the simplicity of the device (a single rectangular channel) is allows the system to be easily parallelized in order to further enhance the throughput.

Figure 14:
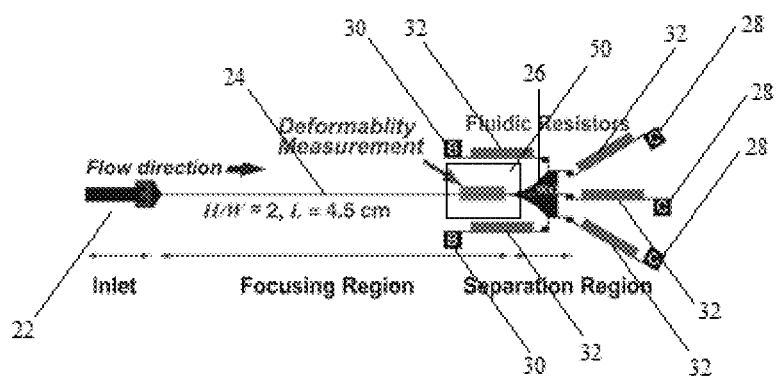
FIG. 14 is a top schematic view of a particle analyzing system including an inertial focusing microchannel according to one embodiment of the invention.

FIG. 14 is a schematic view of a particle analyzing system according to one embodiment of the invention. The system in FIG. 14 is similar to the microfluidic device in FIG. 1d, except that a particle analyzer 50 has been added to the straight focusing channel 24 of the microchannel 34. The analyzer 50 is disposed relative to the straight focusing channel 24 to be able to detect separation along the width of the microchannel 34. The analyzer 50 can be a high-speed imager, a laser excitation device, or any other device capable of detecting particle separation. The particle position information from the analyzer 50 is used to categorize particles flowing through the particle analyzing system. Although the particle analyzing system is depicted with an expanding region 26, such a region is not required for a particle analyzing system.

Enrichment of Cancer Cells in Peripheral Blood

Blood cell suspensions containing cancer cells or other particles are injected into the DACS device in order to separate and enrich cancer cells/particles. Deformability activated cell sorting (enrichment) can be achieved when the sample injection flow rate is maintained with the syringe pump to have channel Reynolds number, $$R_c = \frac{\rho U_m W}{\mu},$$

ranging from about 10 to about 40. Here, ρ, $U_m$, μ are density, maximum velocity, viscosity of the fluid, respectively. Further, a and W are particle diameter and channel width, respectively. For example, flow rates corresponding to Reynolds number, $R_c$=21 and 42, and different fluidic resistances can be used. Fractions can be collected from two outer outlets for enrichment of blood cells and three inner outlets for enrichment of cancer cells. In this $R_c$ range the difference between blood and cancer cell equilibrium positions is maximized, while maintaining high yield and throughput.

Applications for enrichment of circulating tumor cells, rare cancer stem cells, fetal cells in maternal blood, or other rare cells are possible. Also, enrichment of cells or microorganisms in dilute fluids like urine, or water may benefit from this approach.

Passive Label-Free Enrichment of Spiked Cancer Cells in Dilute Whole Blood.

Figure 4A:
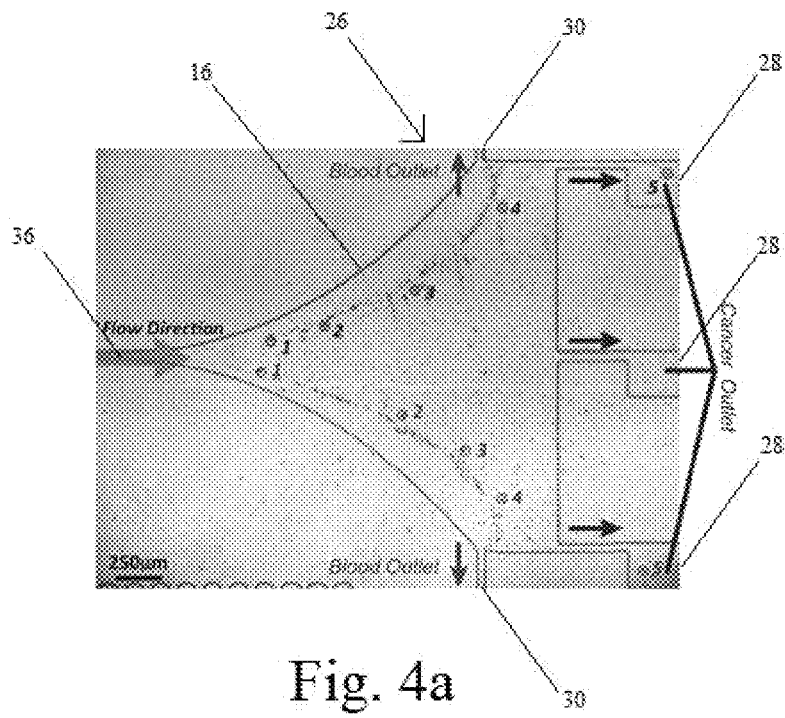
FIG. 4a is a top view of an expanding region of a microchannel constructed from sequences of high-speed microscopy images according to one embodiment of the invention.
Figure 4B:
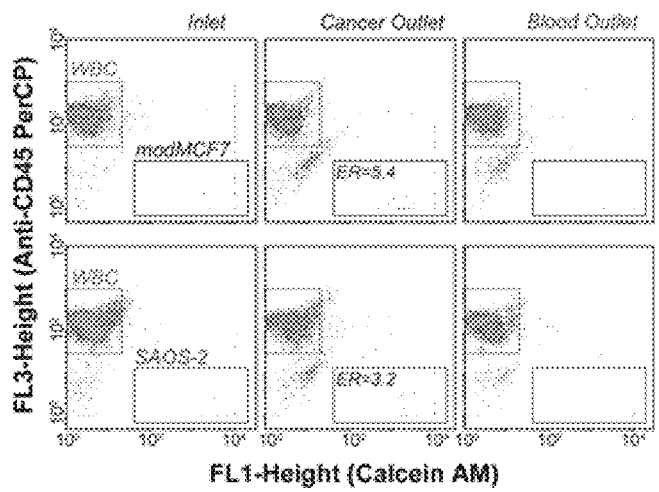
FIG. 4b is a plot of FL3 height versus FL1 height showing flow cytometry data.

The significant differences in lateral equilibrium position between cancer and blood cells can be used in label-free enrichment and collection of such cells (FIG. 4a). FIG. 4b shows the cellular components at the inlet and the fractions from the blood and cancer outlets. The maximum enrichment ratio for both modMCF-7 and SAOS-2 cells is found at $R_c=21$ with modified fluidic resistances at the blood outlets (0.1% reduction in overall fluidic resistance). In agreement with $X_{eq}$ measurements (FIG. 3a), more deformable metastatic breast cancer cells (e.g., modMCF7) have a better enrichment ratio than osteosarcoma cells (e.g., SAOS-2). Metastatic breast cancer cells are enriched by a factor of approximately 5.4 with about 96% recovery of target cells at the collection outlets while osteosarcoma cells were enriched by a factor of approximately 3.2X with about 97% yield.

Figure 4C:
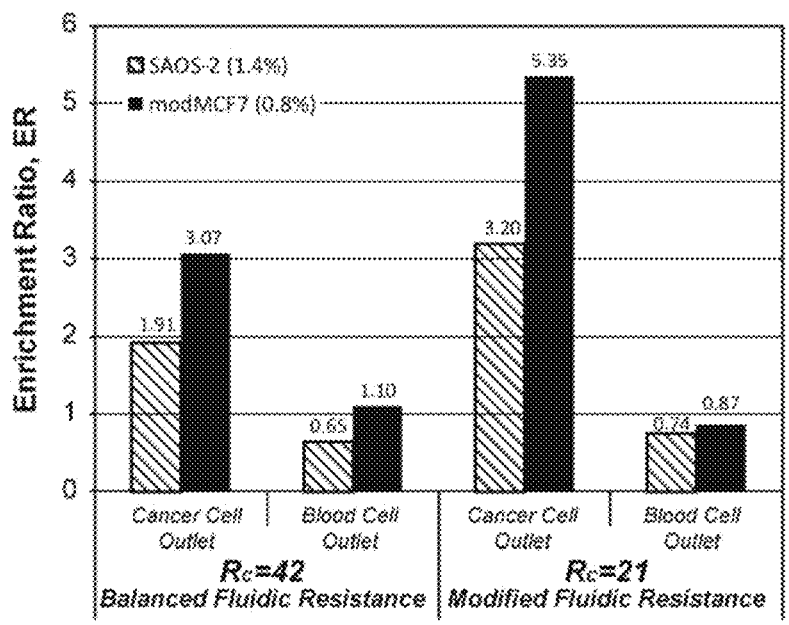
FIG. 4c is a bar graph of the enrichment ratios of samples collected at various outlets of a system according to one embodiment of the invention under various flow conditions.

FIG. 4a-FIG. 4c illustrate passive label-free deformability-activated cell enrichment. FIG. 4a shows an image of the separation outlet, constructed from sequences of high-speed microscopy images with a time interval of 33 ms. Vertical and horizontal arrows indicate the outlets for suspensions enriched in blood cells and suspensions enriched in cancer cells, respectively. Individual cancer cells separated from the mixture are marked with numbered circles. FIG. 4b depicts flow cytometry data showing that the cell populations in the initial sample and those collected from the cancer and blood outlets are different. By comparing the "inlet" panels with the "cancer outlet" panels, it is qualitatively apparent that the sample flowing through the cancer outlet contains more cancer cells than those flowing through the inlet or the blood outlet. FIG. 4c shows a comparison of enrichment ratios for modMCF7 and SAOS-2 cells at varied flow conditions is shown. The initial fraction of the cancer cells (modMCF7 and SAOS-2) to leukocytes was 0.8% and 1.4%, respectively. FIG. 4c shows that fractions of cancer cells (modMCF7 and SAOS-2) to leukocytes increases to 3.07% and 1.91%, respectively for $R_c=42$, and 5.35% and 3.20%, respectively for $R_c=21$.

The throughput of a single device is ~22,000 cells/min when the device is operated at $R_c=42$. Although this throughput is slower than conventional rare cell enrichment systems, the approach is label-free and does not require complex, additional electrical/optical components as other active, label-free target cell separation techniques do. Additionally, throughput can be further improved by parallelizing the device. With parallelization of 45 single-devices, 1 ml of RBC-lysed blood (~8 million WBCs) is expected to be processed within 8 min. Moreover, owing to the simplicity of the device (e.g., a single-layer device with one input and no additional external force requirements) and high yield, the system can be easily cascaded in series in order to achieve higher levels of enrichment without significant sample loss.

The system is also very robust, being operating stably for >3 hours without clogging or intervention due to innovations in microfluidic design (including low shear transitions that prevent cell rupture and clogging and high-impedance outlets which maintain flow rate uniform with small clogs). Moreover, the system may be integrated upfront to state-of-the-art image based target cell detection systems or FACS in order to enhance the overall throughput by reducing the RBC/WBC background.

Global Gene Expression and Cell Viability of MCF7 Cancer Cells

Flowing cells through the above-described DACS device does not significantly alter global gene expression (through, for instance, shear stress). MCF7 cells flowed through the DACS device at $R_c=21$ for 3 hours were compared with control MCF7 cells using global gene expression and cell viability assays.

Figure 5A:
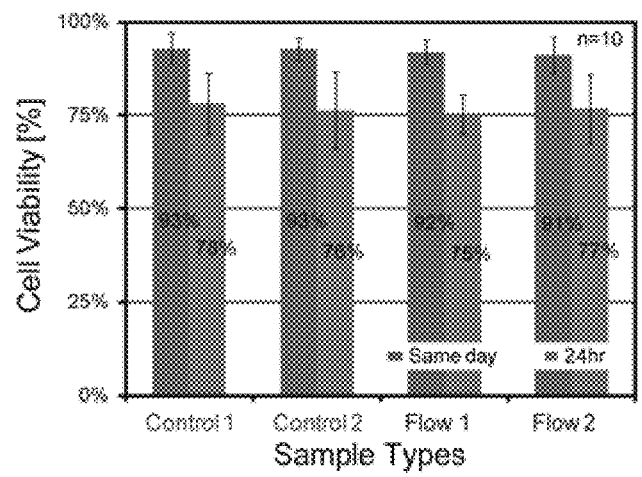
FIG. 5a is a bar graph of the cell viability of various samples, some of which have been flowed through a system according to one embodiment of the invention.
Figure 5B:
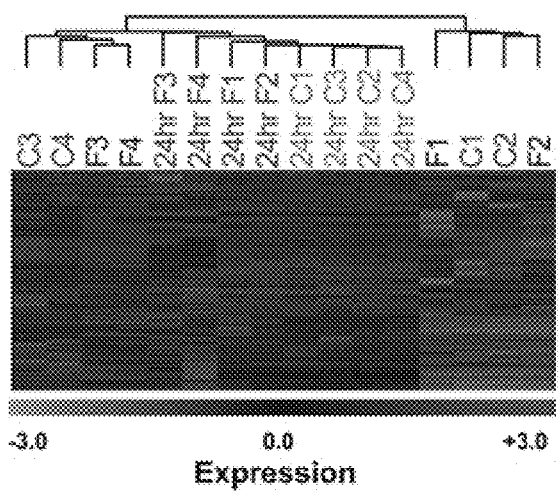
FIG. 5b is an unsupervised hierarchical clustering dendrogram of microarray data for gene expression in MCF7 cells.

FIGS. 5a-5b demonstrate that inertial focusing does not significantly affect cell viability and gene expression. FIG. 5a is a bar graph depicting the results of viability tests showing that cells flowed through the device remain highly viable similar to control cells not flowed through the system. FIG. 5b shows unsupervised hierarchical clustering of microarray data for MCF7 cells for 8 control (C1, C2, C3, C4, 24 hr C1, 24 hr C2, 24 hr C3, 24 hr C4) and 8 flow conditions (F1, F2, F3, F4, 24 hr F1, 24 hr F2, 24 hr F3, 24 hr F4). The total number of annotated genes depicted in FIG. 5b is 364. FIG. 5b illustrates that the processed cells do not have distinct global gene expression compared to control samples. All FIGS. in this application are describe in detail in *Deformability-based cell classification and enrichment using inertial microfluidics*, Hur S. C., Henderson-MacLennan N. K., McCabe E. R. B., and Di Carlo, D., *Lab on a Chip*, 2011(11), 912-920 and the supporting information therefore, which are both incorporated by reference.

Gene Expression and Cell Viability is not Significantly Affected by Inertial Separation.

Figures 9A, 9B:
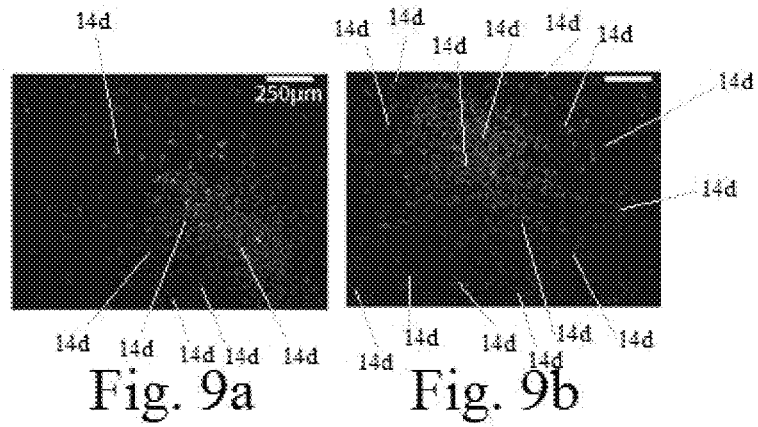
FIG. 9a-FIG. 9b are fluorescent microscopy images of MCF7 cells.
Figures 9C, 9D:
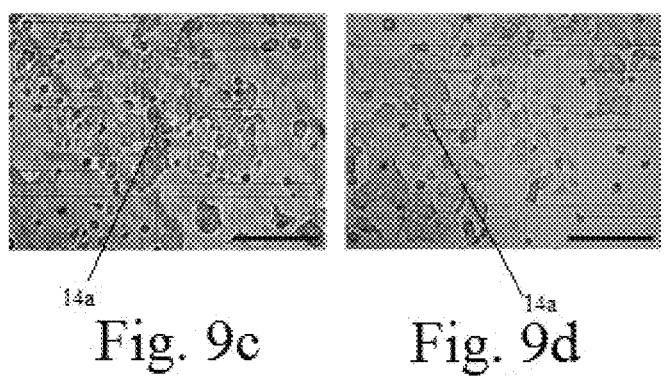
FIG. 9c-FIG. 9d are microscopy images of MCF7 cells.

The overall gene expression profile of MCF7 cells before and after flow through the system shows only minor changes and the processed cells remain highly viable and proliferated for over a week (see FIGS. 9a-9c). Unsupervised clustering using the 364 most varying annotated genes (2035 probe sets) was performed to determine whether cells flowed through the device have globally distinct gene expression profiles since (i) not all of the 2035 probe sets have annotations and (ii) the same clustering pattern seen in the 364 gene list is observed with the 2035 gene list. Hierarchical clustering showed that control and flow samples (C and F) and 24 hour samples were clustered together (see FIG. 5b), indicating that the gene expression profiles for processed MCF7 cells were not globally distinct from the control samples.

FIGS. 9a-9d illustrate processed cancer cells remaining highly viable. Fluorescent microscopic images of control MCF7 cells 14a (FIG. 9a) and MCF7 cells 14a flowed through the microfluidic system (FIG. 9b), both stained with Calcein AM/Ethidium homodimer-2. FIG. 9b contains dead cells 14d (stained red) among live cells 14c (stained green). Microscopic images of control (FIG. 9c) and processed (FIG. 9d) MCF7 cells 14a at day 7. Both cells 14a were plated on petri-dishes with grids (ibidi®) and cultured for a week. Flowed cells 14a proliferated well and possessed a similar morphology as the control sample. Scale bars are 250 µm.

Moreover, gene filtering between control (C1-C4) and flow (F1-F4) samples collected at the same day of processing using a t-test ($p<0.05$) and the fold-change criterion (2 fold-change) showed that no single gene was differentially expressed between those samples. However, gene filtering analysis (2 fold-change) of 24 hour samples revealed one probe set without an annotated gene name that was up-regulated in 24 hour flow samples compared to 24 hour control samples.

Temporal differences revealed 46 and 69 probe sets corresponding to 27 (gene list 1) and 25 (gene list 2) Affymetrix-annotated genes, that were differentially expressed between C and 24 hr C, and F and 24 hr F, respectively. Of these, twenty-seven probe sets/16 annotated genes (gene list 3) overlapped between C versus 24 hr C and F versus 24 hr F. These three gene lists were used for hierarchical clustering dendrograms (FIGS. 10a-10c) and imported into the Ingenuity program for pathway analysis.

Figures 10A, 10B, 10C:
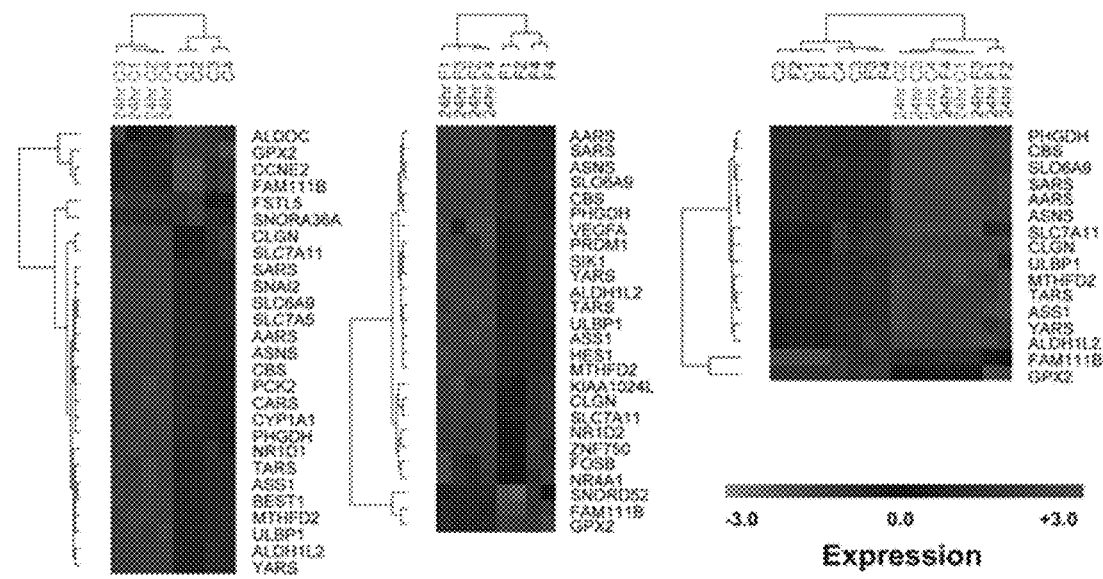
FIG. 10a-FIG. 10c are hierarchical clustering dendrograms of gene lists showing expression.

FIGS. 10a-10c are hierarchical clustering dendrograms of gene lists, which illustrate the temporal difference between control and 24 hour control (FIG. 10a); flowed and 24 hour flowed (FIG. 10b); and control vs. 24 hour control and flow vs. 24 hour flow samples (FIG. 10c). These three gene lists were used for pathway/function analysis.

Figure 11:
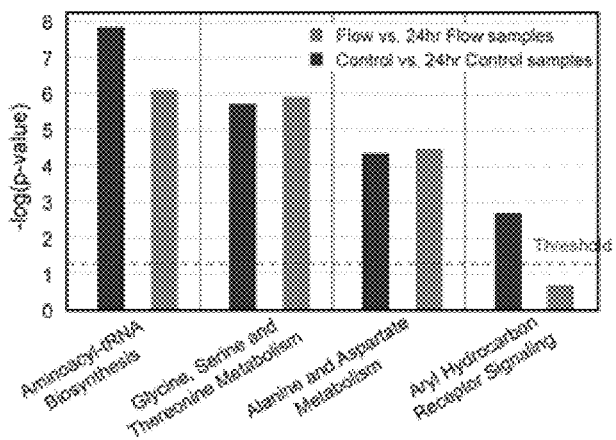
FIG. 11 is a bar graph of gene expression in various pathways.

FIG. 11 depicts pathway analysis of temporal effect on gene expression of MCF7 cells. Three significant canonical pathways were found to be in common in both control vs. 24 hour control and flow vs. 24 hour flow samples, showing that minor alterations in gene expression is independent of flowing cells through the device. Pathway analysis revealed that aminoacyl-tRNA biosynthesis, glycine, threonine and serine metabolism, and alanine and aspartate metabolism were significant canonical pathways in both the C vs. 24 hr C and F vs. 24 hr F samples. Aryl hydrocarbon receptor signaling was a unique canonical pathway in the C vs. 24 hr C samples only (FIG. 11). No significant, non-canonical network pathways or functional enrichment groups were revealed in the C vs. 24 hr C or F vs. 24 hr F comparisons.

Consequently, there are no significant alterations caused by initially flowing cells through the device as evidenced by no statistical differences in gene expression at 2-fold change. Only a limited number of genes in the C vs. 24 hr C and F vs. 24 hr F samples have altered expression after 24 hours of incubation. 27 total/16 annotated genes were in common between C vs. 24 hr C and F vs. 24 hr F samples, indicating that the major subset of the gene expression differences are independent of flow. An important assessment of the temporal effects of flow can be seen in pathway alterations. There is only one pathway difference between C vs. 24 hr C and F vs. 24 hr F samples: aryl hydrocarbon receptor signaling which is a type of toxic and carcinogenic exposure response. In C samples, ⅔ genes in this pathway were down-regulated. The remaining 3 pathways are the same for C vs. 24 hr C and F vs. 24 hr F, further proof of minimal impact of the long-term effects of flowing cells through the device.

Further, the expression profiles of potential genes of interest for development of targeted anticancer therapeutics (MDR1, MRP, LRP, p53) or breast cancer prognostic and clinical stage forecasting (errB-2) were not shown to be differentially expressed between control and experimental samples, which shows that this system may be used to isolate cells for assessment of anticancer drug efficacy and identification of a personalized therapy.

Parallelization

Figure 13:
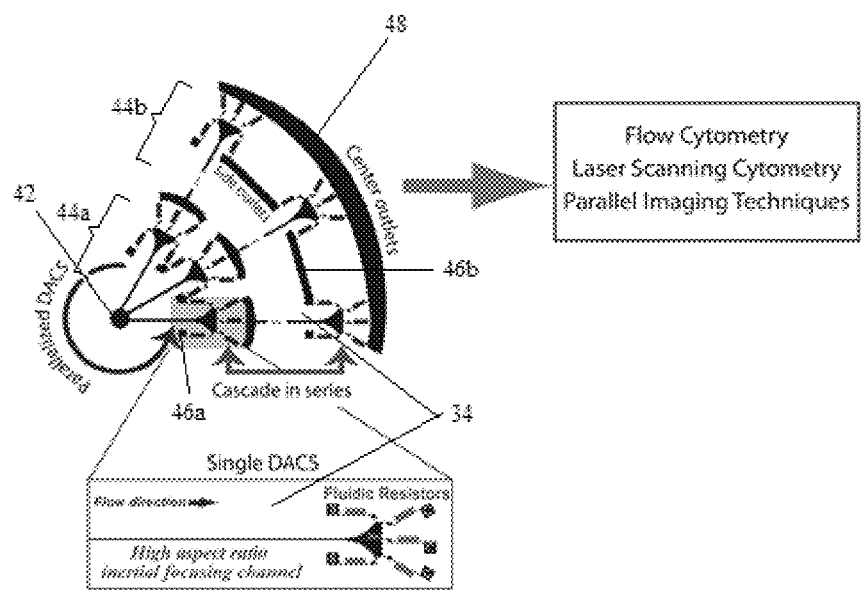
FIG. 13 is a partial top schematic view of a parallelize and serially cascaded DACS systems according to one embodiment of the invention.

Because of the simplicity of the system and high yield, the system can be parallelized and cascaded in series (see FIG. 13). A circular parallelized and serially cascaded system 40 is shown in FIG. 13. The circular system 40 comprises an injection port 42 in the center, concentric loops 44 of microchannels 34, intermediate concentric ring-shaped reservoirs 46, and an outer ring-shaped reservoir 48. Each concentric loop 44 is one microchannel 34 "thick," i.e., the width of each loop 44 is formed by the axial length of a microchannel 34. The injection port 42 is connected to the proximal end of each microchannel 34 in the innermost loop 44a. Some of the intermediate concentric ring-shaped reservoirs 46a are connected to the outer outlets 30 of the microchannels 34 and configured to hold samples flowing therefrom. The inner outlets 28 of the innermost loop 44a are connected to an intermediate concentric ring-shaped reservoir 46a, which is in turn connected to the proximal end of the microchannels 34 in the next concentric loop 44b. The outer ring-shaped reservoir 48 is connected to the inner outlets 28 from the outermost loops 44b and configured to hold samples flowing therefrom. Accordingly, samples flowing through the outer outlets 30 are collected in some of the intermediate concentric ring-shaped reservoirs 46a, 46b and samples flowing through the inner outlets 28 are collected in the outer concentric ring-shaped reservoir 48.

Parallelized and serially cascaded DACS devices have increased throughput and enrichment ratios. Such a parallelized system has the practical throughput to function as a preprocessing unit integrated upfront to a target cell detection system, such as a conventional flow cytometer. Integration of the system upfront to a laser scanning cytometer, or a parallel imaging technique system would further enhance the rare cell detection sensitivity and throughput by eliminating abundant non-target cells (e.g., RBC background). The system can be utilized as an in situ quality control unit for micro-particle synthesis by on-line monitoring the size and mechanical properties of products when the system is integrated with an automated image analysis technique system having a decision making algorithm (e.g., field-programmable gate array (FPGA)) with fast feed-back control.

CONCLUSION

A microfluidic device is capable of passive label-free cell classification and enrichment that uniquely uses cell size and deformability as distinguishing markers. Suspended cells behave much like viscous droplets moving closer to the channel centerline than rigid particles. Consequently, more deformable and larger metastatic cancer cells have lateral equilibrium positions closer to the channel centerline than blood cells, benign cancer, and normal tissue cells from the same origin. Such a device can be incorporated into clinical and research instruments for high-throughput cell classification using cell deformability as a biomarker.

Moreover, a DACS device uses lateral equilibrium position differences to conduct label-free cell enrichment based on cell size and deformability. Such a device has immediate use in lowering the WBC background for imaging-based cell detection. Further improvements in microfluidic design and sequential processing leading to improved enrichment ratios will increase the application areas for this approach Importantly, only minor change in the global gene expression profiles of processed cells renders the proposed technique appropriate for clinical and research applications in which gene expression analysis, or establishment of in vitro culture are desired. Taking advantage of cellular-scale hydrodynamics in inertial flows, the presented systems and techniques have provided cost-effective cell separation and high-throughput deformability measurements of clinical and biological importance. Deformability based cell separation has a large number of potential applications in the field of biological research and medicine, including, but not limited to, the purification of (1) differentiated stem cells from their undifferentiated counterparts, (2) progenitor cells from tissue digestions (e.g., adrenal cortical progenitor cells in adrenal gland), (3) activated leukocytes or Malaria infected blood cells from peripheral blood, and (4) malignant cancer cells (e.g., tumor spheroid and circulating tumor cells) from fine-needle biopsy samples or blood samples.

This technique does not rely on cell labeling with magnetic particles or fluorescent antibodies, which reduces the cost and complexity of processing of blood samples. This provides a low cost diagnostic system for circulating tumor cells or other rare cell enrichment and analysis. Processing with the device is also simple and robust since it operates with a single inlet and outlets with high fluidic resistance. High fluidic resistance minimizes the effects of potential channel obstructions on overall flow through the device and thus enrichment efficiency. Simple device operation and setup also lead to facile parallelization and serialization of the device increasing throughput and enrichment.

Enrichment of Undifferentiated Stem Cells in Stem Cell Cultures

Figure 16A:
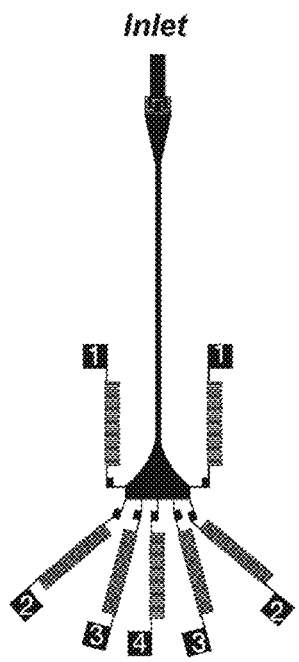
FIG. 16a is a top schematic view of an inertial focusing microchannel according to one embodiment of the invention.
Figure 16B:
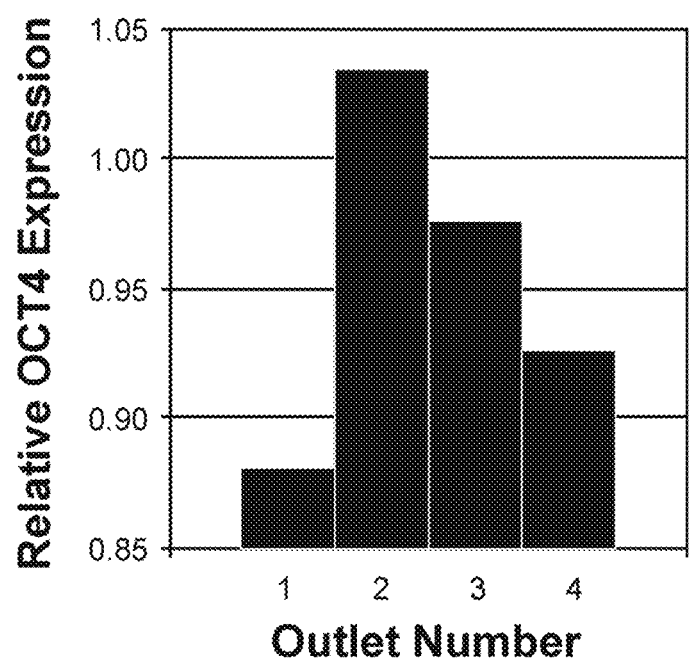

An inertial focusing microchannel (FIG. 16a), similar to the one depicted in FIG. 1d, can be used to enrich undifferentiated human embryonic stem cells ("undiff-hESCs") in stem cell cultures, separating undiff-hESCs from undesired impurity cells (e.g., murine feeder cells and differentiated cells). The more deformable undiff-hESCs are slightly enriched in the inner outlets (outlet 2 through 4), as evidenced by the higher expression of a pluripotency marker (OCT4). FIG. 16b, which shows the relative OCT4 expression level of cells collected from each outlet of the device in FIG. 16a, demonstrates slight enrichment of undiff-hESCs in the inner outlets.

Enrichment of Adrenal Cortical Progenitor Cells in Adrenal Gland Digests

The adrenal cortex is located at the perimeter of the adrenal gland, a major hormone-secreting organ responsible for synthesis of steroid hormones. Growing evidence, supported by numerous anatomic, histologic and regenerative capacity studies, has shown that there is a pool of adrenal cortical progenitor cell ("progenitor cells") in the adrenal cortex, which are potentially capable of continuous and lifelong regeneration of adrenal tissue. Progenitor cells, purified from a patient's own or a healthy donor's adrenal cells, can be expanded in vitro and those progenitor cells can be transplanted to the patient potentially to restore adrenal functionality or to reverse adrenal insufficiency. The purification of such cells, however, has been challenging since only a handful of intracellular molecular markers are available for identification of adrenal cortical progenitor cells.

Fully differentiated adrenal cortical cells have increased intracellular cholesterol content compared to progenitor cells. This difference may originate from differences in the steroid hormone synthesis capabilities of the two cell types. Differentiation of adrenal cortical cells (i.e., variation in intracellular cholesterol content) is associated with clumping of the differentiated adrenal cortical cells, into larger sized clumps. This size difference, in turn, results in distinct lateral equilibrium positions in microscale inertial flow. This difference in lateral equilibrium position between progenitor and differentiated adrenal cortical cells forms the basis of label-free isolation of murine adrenal cortical progenitor cells from adrenal gland digests.

Figure 17A:
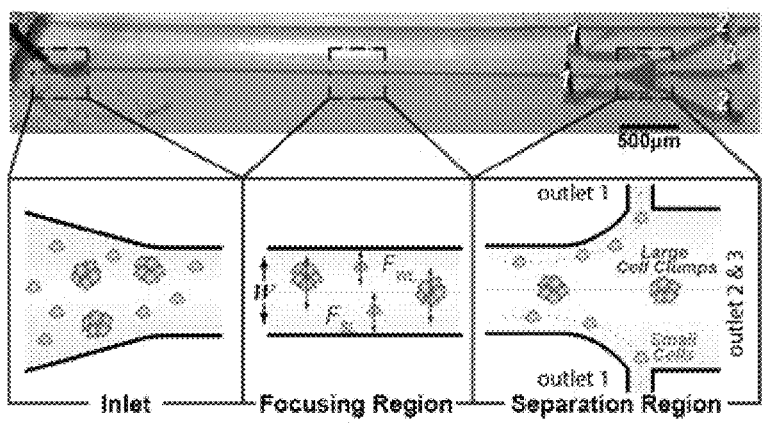
FIG. 17a is a top photograph of an inertial focusing microchannel according to one embodiment of the invention.

FIG. 17a is a top photograph of the microfluidic device used for progenitor cell isolation. FIG. 17b-FIG. 17d are detailed top schematic views showing the inertial focusing of living cell clumps in microscale flow. FIG. 17b shows a solution containing randomly distributed heterogeneous tissue digest, which has been injected at the inlet of the device in FIG. 17a. FIG. 17c shows that flowing cells experience two lateral forces, namely wall effect lift, $F_{WL}$, and shear-gradient lift force, $F_{SL}$, as they travel through the straight focusing region. These forces induce lateral migration of cells and focus them at different locations based on size. Larger cell clusters focus closer to the channel center and smaller individual cells focus closer to the channel walls. FIG. 17d shows differentially focused flowing directed to and collected at designated outlets based on size.

Fluorescence imaging after separation with the device in FIG. 17a showed that cells with little or no cholesterol content (i.e., dim Nile Red intensity in FIG. 18a) were collected at outlet 1, whereas other cell types with higher cholesterol content (i.e., brighter Nile Red intensity in FIG. 18b and FIG. 18c) were enriched at outlets 2 and 3. In addition, cells with higher cholesterol contents were collected in the form of multicellular clusters (FIG. 17c), whereas cells collected in the form of single cells have lower level of cholesterol. Accordingly, more differentiated adrenal cells, which contain higher content of cholesterol, are collected in the form of multicellular clusters at the inner outlets, while the progenitor cells were collected in the form of single cells at the outer outlets. The large size difference among cell types drives the label-free purification of progenitor cells using the device in FIG. 17a.

Figure 18A:
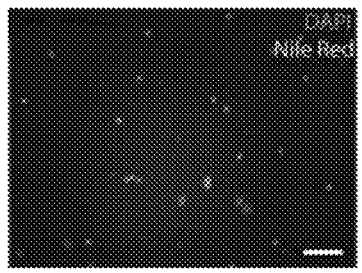
Figure 18B:
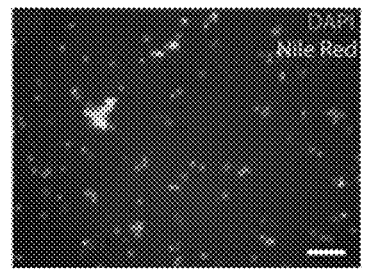
Figure 18C:
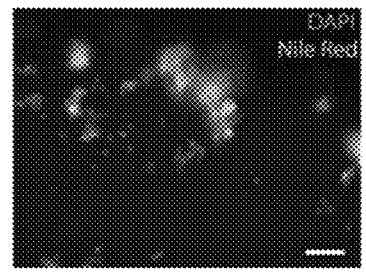

FIG. 18a-FIG. 18c are fluorescent images of cells collected at outlet 1 (FIG. 18a), outlet 2 (FIG. 18b), and outlet 3 (FIG. 18c). These images demonstrate label-free separation of murine adrenal cortical progenitor cells using the device in FIG. 17a. Cells were stained post collection with DAPI (blue) and Nile Red (green) in order to identify nuclei and intracellular lipid droplets, respectively. These figures show significantly lower number of cells (i.e., somatic adrenal cortical cells) expressing high level of lipid droplet contents (Nile Red bright) found in fraction collected from outlet 1 (outer) and the population of Nile Red bright cells was the highest in fraction collected from outlet 3 (inner). Scale bar is 50 µm.

Gene expression measurements also show that outer outlet 1 and inner outlet 3 contain distinctly different cell populations (see FIG. 19). The tissue-specific (but not "zonal-specific," i.e., differentiation specific) gene, Sf1, was expressed with relatively similar level compared to control (not flowed through the device) and experimental groups at all outlets (p=0.9). However, the expression of zonal-specific genes, Cyp11b1 and Cyp11b2, were substantially suppressed for the cells collected from the outer outlet 1, indicating that those cells are at the least differentiated stage (P<0.05). Accordingly, more differentiated multicellular clusters of adrenal cells, expressing higher level of zonal-specific genes (Cyp11b1 and Cyp11b2) are enriched at inner outlets (outlet 2 and 3) while expression level of those genes were significantly lower for the adrenal cortical progenitor cells collected at the outer outlet 1. Asterisks indicateP<0.05 as compared with Nile Red bright cells from outlet 3. Error bar represents standard deviation of measurements from two separate tissue digests.

In addition, processed primary cells were not adversely affected by the inertial flow. The viability of the processed cells is not significantly lower than that of control samples and more than 70% of the cells remained viable 24 hours post processing (see FIG. 20a). Further, the collected samples can be cultured for 10 days in vitro using known protocols. Various cell types with distinct morphology can be observed during the course of the 10-day culture (FIG. 20b). Therefore, purification of target cells from the tissue digest using the device in FIG. 17a would enable further downstream analyses identifying specific culture conditions or new molecular/genetic biomarkers for collected subpopulations.

Utilizing substantial differences in lateral equilibrium positions between single cells and clusters of cells from heterogeneous tissue digests, viable adrenal cortical progenitor cells can be purified in a simple, passive and label-free manner. The throughput of the device in FIG. 17a is around 24,000 cells/min when the device operated at 60

µL/min. Roughly 2 million cells were harvested from 2 adrenal glands and diluted in 5 mL KO media prior to separation. Further, the device does not require labeling and a 10× improvement in throughput can be achieved using the above-described parallelization of the device. Moreover, higher level of purity for collected progenitor cells can be achieved by cascading the devices in series. Moreover, the current system is capable of autonomously and stably operating for more than 3 hours while maintaining uniform flow at all outlets. Cell death can be reduced by including low-shear-transition designs, minimizing cell rupture and cross-contamination.

The inertial focusing microchannel device shown in FIG. 17a enriches adrenal cortical progenitor cells from adrenal gland digests. Adrenal cortical progenitor cells with little to no cholesterol content can be isolated in the form of single cells at the outer outlets, whereas more differentiated adrenal cells with higher cholesterol content can be collected as multicellular clusters at the inner outlets.

While embodiments have been shown and described, various modifications may be made without departing from the scope of the inventive concepts disclosed herein. The invention(s), therefore, should not be limited, except to the following claims, and their equivalents.

What is claimed is:

1. A method of characterizing cancer cells within a population of other cells using image analysis software and a microfluidic device comprising:

flowing a fluid including cancer cells and other cells suspended therein through an inertial focusing microchannel of width (W) disposed in a substrate of the microfluidic device and having an upstream end and a downstream end, the cancer and other cells approximating the shape of a sphere of diameter (a) within the flowing fluid, resulting in focused cancer cells and other cells and wherein the downstream end contains the focused cancer and other cells;

imaging the focused cancer and other cells with an imaging device at a measurement location within the inertial focusing microchannel, the measurement location located at the downstream end of the inertial focusing microchannel;

measuring with the image analysis software the lateral equilibrium positions ($X_{eq}$) of the cancer and other cells at the measurement location based on images obtained from the imaging device by measuring the distance of a center of each cancer and other cell from a wall of the inertial focusing microchannel at the measurement location, resulting in measured lateral equilibrium positions ($X_{eq}$) of each of the cancer and other cells;

comparing the measured lateral equilibrium positions ($X_{eq}$) of the cancer and other cells against a threshold lateral equilibrium position ($X_{eq}$); and identifying the cancer cells from the other cells based on whether the measured lateral equilibrium position ($X_{eq}$) of measured cells was above a threshold lateral equilibrium position ($X_{eq}$) of 0.6 for a cell diameter to microchannel width ratio (a/W) of 0.2 and above a threshold lateral equilibrium position ($X_{eq}$) of 0.8 for a cell diameter to microchannel width ratio (a/W) of 0.5 and linear values therebetween.

2. The method of claim 1, further comprising measuring size of the cancer and other cells obtained from the imaging device and wherein each of the cancer and other cells is further characterized based at least in part on the measured size and the measured lateral equilibrium position ($X_{eq}$).

3. The method of claim 1, further comprising measuring shape deformation of the cancer and other cells from the imaging device and wherein each of the cancer and other cells is further characterized based at least in part on the shape deformation and the measured lateral equilibrium position ($X_{eq}$).

4. The method of claim 2, further comprising characterizing the cancer and other cells based on whether the measured size is above or below a size threshold value.

5. The method of claim 1, further comprising sorting the cancer and other cells into a plurality of outlets, wherein one outlet contains enriched concentrations of cancer cells.

6. The method of claim 1, wherein the cancer cells comprise cancer cells with increased metastatic potential and the other cells comprise cancer cells with reduced metastatic potential.

7. The method of claim 1, wherein the imaging device comprises a camera.

8. The method of claim 1, wherein the imaging device comprises a laser-based device.

9. The method of claim 1, wherein the microchannel has a height and width dimensioned such that the height to width ratio is ≥2, and wherein the lateral equilibrium position ($X_{eq}$) is measured along the width dimension.

10. The method of claim 1, wherein the fluid is flowed through the inertial focusing microchannel such that the Reynolds number ($R_c$) is less than 27.

11. The method of claim 1, wherein the cancer and other cells are label-free.

* * * * *